United States Patent [19]

King et al.

[11] 4,308,261
[45] Dec. 29, 1981

[54] SUBSTITUTED OXADIAZOLES AND THEIR USE AS WIRE WORM AND FLEA BEETLE INSECTICIDES

[75] Inventors: William F. King, Novato; Ronald E. Wheeler, Martinez, both of Calif.

[73] Assignee: Chevron Research, San Francisco, Calif.

[21] Appl. No.: 143,567

[22] Filed: Apr. 25, 1980

[51] Int. Cl.³ .................. A01N 57/00; A01N 57/26
[52] U.S. Cl. ................................................. 424/200
[58] Field of Search ........................................ 424/200

[56] References Cited

U.S. PATENT DOCUMENTS

| 3,432,519 | 3/1969 | Metivier et al. | 424/200 |
| 3,709,902 | 1/1973 | Boyce et al. | 424/200 |
| 4,110,336 | 8/1978 | Mildenberger et al. | 424/200 |

FOREIGN PATENT DOCUMENTS

| 1451294 | 2/1966 | France | 424/200 |
| 44-24600 | 10/1969 | Japan | 424/200 |
| 48-1136 | 9/1973 | Japan | 424/200 |
| 51-9007 | 3/1976 | Japan | 424/200 |

*Primary Examiner*—Douglas W. Robinson
*Attorney, Agent, or Firm*—J. A. Buchanan, Jr.; D. A. Newell; T. G. DeJonghe

[57] ABSTRACT

A method for killing wire worms and flea beetles which comprises applying to the soil habitat of the wire worms and flea beetles an insecticidally effective amount of a compound of the formula

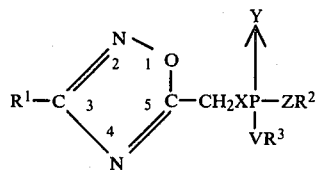

wherein $R^1$, $R^2$ and $R^3$ are alkyl of 1 to 4 carbon atoms; and X, Y, Z and V are sulfur or oxygen.

6 Claims, No Drawings

SUBSTITUTED OXADIAZOLES AND THEIR USE AS WIRE WORM AND FLEA BEETLE INSECTICIDES

BACKGROUND OF THE INVENTION

The present invention relates to certain oxadiazole derivatives and their use as wire worm and flea beetle insecticides.

British Pat. No. 1,213,707 discloses insecticidal compounds of the general formula

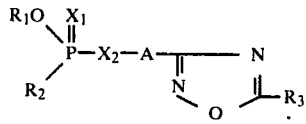

wherein $X_1$ and $X_2$, which may be the same or different, each represents an oxygen or sulfur atom; A represents an alkylene group; $R_1$ represents an alkyl group, $R_2$ represents an alkyl or alkoxy group; and $R_3$ represents a hydrogen atom or an optionally substituted carbamoyl or amino group. A particular species disclosed in the British Patent at Table 2, 9th compound from the top, is 3-(diethoxyphosphinothioylthiomethyl)-5-methyl-1,2,4-oxadiazole.

The examples of the British Patent show testing of certain of the compounds for insecticidal activity on adult houseflies; mosquito larvae, diamond back moth larvae, aphids and adult mustard beetles; red spider mites; and white butterfly larvae. None of these tests involved application and use of the insecticide in the soil habitat of the insects.

U.S. Pat. No. 4,028,377 discloses insecticidal compounds of the general formula

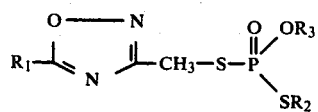

wherein $R_1$ represents hydrogen, unsubstituted alkyl, benzyl or phenyl, $R_2$ represents methyl or ethyl, and $R_3$ represents unsubstituted $C_1$-$C_7$ alkyl optionally interrupted by oxygen or represents $C_3$-$C_4$ alkenyl.

The examples of the U.S. Pat. No. 4,028,377 patent show testing of certain of the compounds for insecticidal activity on ticks in cotton wool; larvae of ticks; mites; and on root-gall-nematodes in soil. In the latter test, the soil infested with the root-gall-nematocides was treated with the compounds to be tested and then tomato seedlings were planted either immediately after the soil preparation or after 8 days waiting.

British Pat. No. 1,261,158 discloses compounds of the general formula

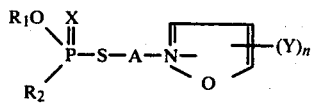

The first compound disclosed in Table I of British Pat. No. 1,261,158 is 5-(diethoxyphosphinothioylthiomethyl)-3-methylisoxazole. The compounds of the examples of British Pat. No. 1,261,158 were tested for insecticidal effectiveness on flies, mosquito larvae, moth larvae, mustard beetles, aphids, spider mites and butterfly larvae.

U.S. Pat. No. 3,432,519 discloses various oxadiazoles with phosphate groups in the 5-position on the oxadiazole ring. Example 2 discloses 3-methyl-5-chloromethyl-1,2,4-oxadiazole. U.S. Pat. No. 3,432,519 in Example 4 discloses that the last-named compound is used to destroy green flies, red spiders and caterpillars.

As described in the Ortho Seed Treater Manual copyright 1976, Chevron Chemical Company, page 27, wire worms have been controlled with a formulation comprising a mixture of Lindane (gamma isomer of benzene hexachloride) and Captan (n-[(trichloromethyl)thio]-4-cyclohexene-1,2-dicarboximide).

SUMMARY OF THE INVENTION

According to the present invention, there is provided a method for killing wire worms and/or flea beetles which comprises applying to the soil habitat of the wire worms and/or flea beetles an insecticidally effective amount of a compound of the formula

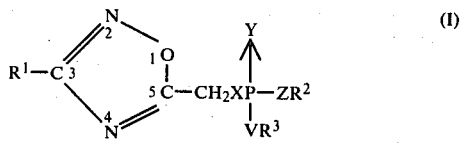

wherein $R^1$, $R^2$ and $R^3$ are alkyl of 1 to 4 carbon atoms; and X, Y, Z and V are sulfur or oxygen.

Preferred compounds for use in this method include those wherein $R^2$ and $R^3$ are ethyl and, more preferably, wherein the compound is further defined in that Y is sulfur and Z and V are oxygen. Most preferably, the compound used is one wherein the compound is still further defined in that $R^1$ is methyl and X is sulfur.

According to another alternative embodiment of the present invention there is provided a wire worm and/or a flea beetle insecticidal composition comprising a wire worm- and/or a flea beetle-insecticidically effective amount of a compound of the formula I, wherein $R^1$, $R^2$ and $R^3$ are alkyl of 1 to 4 carbon atoms; and X, Y, Z and V are sulfur or oxygen; and a biologically inert carrier. Preferably, the compound used in this embodiment of the present invention is 3-methyl-5-(diethoxyphosphorothioylthiomethyl)-1,2,4-oxadiazole.

The term "wire worm" is used herein to include the larvae of click beetles and also to include "False wire worms". Click beetles are in the family Elateridae and the following genera in the Elateridae family are particularly preferred genera for the insecticidal method of the present invention: Melantus, Ctenicera, Conoderus, Limonius, Horistonotus, and Agriotes. False wire worms are in the family Tenibrionidae. The following genera in the Tenibrionidae family are particularly preferred genera against which the insecticidal method of the present invention is used: Eleodes, Blapstinus, and Embaphion.

The term "flea beetle" is used herein to mean the larvae of flea beetles of the family Chrysomelidae. The following genera in the Chrysomelidae family are particularly preferred genera against which the insecticidal method of the present invention is used: Chaetocnema, Epitrix, Phyllotreta, and Systena.

The compounds of the present invention may be prepared by subjecting 3-alkyl-5-chloromethyl-1,2,4-oxadiazoles (II) to a phosphorylation reaction.

The 3-alkyl-5-chloromethyl-1,2,4-oxadiazoles (II) were prepared by condensing the appropriate alkylamidoximes (obtained from nitriles—see Chem. Revs. 61 155 (1961) with chloroacetyl chloride.

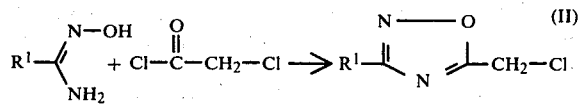

The 3-alkyl-5-chloromethyl-1,2,4-oxadiazoles were phosphorylated with phosphate salts of the general formula (III) to give (I) above:

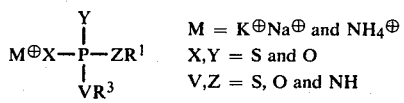

$M = K^{\oplus}Na^{\oplus}$ and $NH_4^{\oplus}$
$X,Y = S$ and $O$
$V,Z = S, O$ and $NH$ This last reaction can be carried out in a number of solvents, e.g., acetone, acetonitrile, ether, methanol, benzene, etc. Preferably, equimolar amounts of reactants are employed, although a small excess of either may be employed. Either reactant may be added to the other reactant in the solvent; however, it is preferred to add the solid phosphate salt to a solution of the 3-alkyl-5-chloromethyloxadiazole. The addition is carried out at temperatures in the range of 15°–30° C. Upon completion of addition of the salt, the temperature of the reaction is raised, preferably to the reflux temperature. The reaction is generally complete in 1–5 hours. At completion of the reaction, the product reaction mixture is filtered to remove any insoluble salts. The filtrate is then stripped of solvent under reduced pressure to give crude 3-alkyl-5-(dialkoxyphosphorothioylthiomethyl)-1,2,4-oxadiazole. The crude material can be purified by column chromatography (silica gel) and eluting with hydrocarbons and chlorinated hydrocarbons.

EXAMPLE 1—PREPARATION METHODS (a) Acetamidoxime—Acetonitrile was added to a previously stirred solution of 0.55 mol hydroxylamine hydrochloride and 0.55 mol anhydrous sodium carbonate in 750 ml of absolute ethanol. This mixture was stirred for 0.5 hour at room temperature and then refluxed at 55°–70° C. for 24 hours. The reaction was cooled and filtered, the solid residue slurried in warm acetone and refiltered, the filtrates were combined and concentrated to an oil under reduced pressure. The oil was again taken up in acetoneether to rid the system of dissolved inorganic salts. The acetone-ether filtrate was concentrated under reduced pressure, the oil was then triturated with ether-hexane leaving a white solid. Infrared (IR) and nuclear magnetic resonance (NMR) elemental analysis indicated the acetamidoxime (m.p. 128°–133° C.).

(b) 3-Methyl-5-Chloromethyl-1,2,4-Oxadiazole—Acetamidoxime (14.1 g) was placed in 200 ml of benzene in a 3-necked, round-bottom flask equipped with a mechanical stirrer, condenser and dropping funnel charged with 23 g of chloroacetyl chloride. The benzene slurry was increased in temperature to near reflux, and the chloroacetyl chloride was added dropwise to the refluxing mixture. A Dean-Stark trap was added and refluxing continued for 3 hours. The reaction mixture was cooled and 100 ml benzene added, washed (3×125 ml) with water, dried with anhydrous MgSO₄, and solvent removed under reduced pressure, leaving the desired product as an amber liquid (confirmed by IR, NMR and elemental analysis).

(c) 3-Methyl-5-(diethoxyphosphorothioylthiomethyl)-1,2,4-oxadiazole—3-methyl-5-chloromethyl-1,2,4-oxadiazole (0.04 mol) was dissolved in acetone and ammonium, O,O-diethyldithiophosphate (0.04 mol) was added with stirring in several portions. The reaction was then refluxed for 3 hours, cooled and filtered. The solvent was removed under reduced pressure leaving an amber oil which was chromatographed (silica gel) and eluted with hexane: methylene chloride (80%). The phosphate was obtained as an almost colorless oil.

EXAMPLE 2—COMPOUND TESTING AGAINST WIRE WORMS AND FLEA BEETLES LARVAE

A granule containing 10% by weight of 3-methyl-5-(diethoxyphosphinothioylthiomethyl)-1,2,4-oxadiazole (the test compound) was distributed in the test field by a broadcast method. The field was then disced to incorporate the granules to a depth of 4 to 5 inches in the soil. Dosage was at 3, 2, and 1 pound test compound per acre.

Next Julian Sweet potatoes were transplanted into the treated plots known to be infested with wire worms (Conoderus vespertinus and C. auritus), and flea beetles larvae (Systena elongata). Four months later, the sweet potatoes were harvested and were graded for number of roots damaged and/or scarred by wire worms and flea beetle larvae. The results are given in Table I.

TABLE I

| Test Compound and Dosage | Roots Damaged By Wire Worms | Roots Scarred By Wire Worms | Roots Damaged By Flea Beetle Larvae | Roots Scarred By Flea Beetle Larvae |
|---|---|---|---|---|
| Test compound | | | | |
| 1 pound/acre | 3.3 | 11.3 | 5.0 | 17.3 |
| 2 pounds/acre | 4.3 | 13.3 | 3.7 | 10.3 |
| 3 pounds/acre | 1.3 | 3.0 | 1.0 | 2.3 |
| No treatment | 7.3 | 20.3 | 10.0 | 35.7 |
| Furadan insecticide 3 pounds/acre | 2.0 | 4.3 | 0.7 | 2.0 |

(1) The test results are the mean of 3 replicas and are based in examining 25 roots.

What is claimed is:
1. A method for killing wire worms or flea beetles which comprises applying to the soil habitat of the wire worms or flea beetles an insecticidally effective amount of a compound of the formula

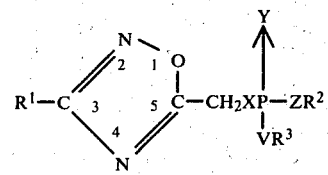

wherein $R^1$, $R^2$ and $R^3$ are alkyl of 1 to 4 carbon atoms; and X, Y, Z and V are sulfur or oxygen.

2. A method in accordance with claim 1 wherein $R^2$ and $R^3$ are ethyl.

3. A method in accordance with claim 2 wherein Y is sulfur and Z and V are oxygen.

4. A method in accordance with claim 3 wherein $R^1$ is methyl and X is sulfur.

5. A method in accordance with claim 4 wherein the insects killed are wire worms of the Elateridae family.

6. A method in accordance with claim 5 when the wire worms killed belonging to the genera Melanthus, Ctenicera, Conoderus, Limonius, Horistonotus, and Agriotes.

* * * * *